(12) United States Patent
Hardy et al.

(10) Patent No.: US 7,293,665 B1
(45) Date of Patent: Nov. 13, 2007

(54) OVEN-SUPPORTABLE CANNING IMPLEMENT STERILIZATION RACK

(76) Inventors: Beverly Ann Hardy, 9521 ECR 6700, Slaton, TX (US) 79364; Lillie Jo Young, 4608 37th St., Lubbock, TX (US) 79414

( * ) Notice: Subject to any disclaimer, the term of this patent is extended or adjusted under 35 U.S.C. 154(b) by 438 days.

(21) Appl. No.: 10/997,900

(22) Filed: Nov. 29, 2004

(51) Int. Cl.
*A47F 5/08* (2006.01)
*B47F 3/14* (2006.01)

(52) U.S. Cl. .................. 211/153; 211/41.4; 211/74; 211/133.5

(58) Field of Classification Search ............... 211/153, 211/181.1, 41.4, 74, 41.3, 76, 84, 83, 90.3, 211/106, 126.9, 133.2, 133.5, 133.6, 134; 34/237, 238, 202; 422/300–303, 292, 297
See application file for complete search history.

(56) References Cited

U.S. PATENT DOCUMENTS

| | | | |
|---|---|---|---|
| 1,344,252 A | 6/1920 | Baehr | |
| 1,618,622 A * | 2/1927 | Woolsey | 211/74 |
| 2,597,407 A | 5/1952 | Thompson | |
| 3,347,618 A * | 10/1967 | McKeown | 422/302 |
| 3,460,899 A * | 8/1969 | Miller | 422/300 |
| 3,800,957 A * | 4/1974 | Krause | 211/41.3 |
| 3,875,854 A | 4/1975 | Wassenaar | |
| 4,350,253 A | 9/1982 | Rusteberg | |
| 4,505,393 A | 3/1985 | Fleigle et al. | |
| 4,621,739 A * | 11/1986 | Heymann et al. | 211/74 |
| 4,756,582 A * | 7/1988 | Heien | 312/229 |
| 4,830,200 A * | 5/1989 | Zambano et al. | 211/133.5 |
| 5,092,311 A * | 3/1992 | Ririe | 126/25 R |
| 5,133,463 A * | 7/1992 | Merl | 211/190 |
| 5,213,776 A | 5/1993 | Maniero et al. | |
| 5,441,707 A * | 8/1995 | Lewis et al. | 422/300 |
| 5,927,267 A * | 7/1999 | McKenzie | 126/41 R |
| 6,179,134 B1 * | 1/2001 | Pine et al. | 211/41.3 |
| 6,726,038 B2 * | 4/2004 | Ko | 211/153 |
| 6,745,906 B1 | 6/2004 | Nagel | |
| 6,766,730 B2 * | 7/2004 | Wrenn | 99/345 |
| 6,886,702 B2 * | 5/2005 | Trinidad et al. | 211/181.1 |
| 6,902,072 B2 * | 6/2005 | Douglas | 211/70.7 |
| 2003/0124024 A1 * | 7/2003 | Chang | 422/22 |

* cited by examiner

*Primary Examiner*—Jennifer E. Novosad
(74) *Attorney, Agent, or Firm*—Jones, Tullar & Cooper, P.C.

(57) ABSTRACT

A canning implement sterilization rack includes a canning jar receiving grid, a ring or band receiving receptacle and a water bath which is supported in a cradle. The rack is adapted to be supported in an oven and is adjustable in width so that it can be used with a variety of oven sizes. In use, the rack's three areas each receive their intended ones of the canning implements. The rack is placed in an oven and is heated for a time sufficient to sterilize the components.

21 Claims, 4 Drawing Sheets

OVEN-SUPPORTABLE CANNING IMPLEMENT STERILIZATION RACK

FIELD OF THE INVENTION

The present invention is directed generally to a canning implement sterilization rack. More specifically, the present invention is directed to an oven-supportable canning implement serialization rack. Most specifically, the present invention is directed to a size adjustable, oven supportable canning implement sterilization rack. The various canning implements, such as canning jars, bands, and seals which are typically used in home canning or in the preserving of perishable food items, are able to be sterilized by being subjected to elevated temperature in a conventional oven. A sterilization rack that is adapted for such usage includes a plurality of jar holding compartments. A band support area will receive a plurality of the jar engaging bands. The seals, which are held on the jar mouth by the bands, are supported in a water bath portion of the rack. The sterilization rack is size adjustable and is supportable on the slide rails of a typical domestic oven.

BACKGROUND OF THE INVENTION

Home canning or preserving of perishable food items is a popular method for enabling a person to store items that otherwise would spoil, if not subjected to refrigeration or freezing. As is known to those who enjoy home canning, it is of the upmost importance that the canning implements; i.e. the jars, bands and seals be sterilized before they are used. Since home canning utilizes heat to attain such a sterile condition of the canning implements, this heating has typically required the use of a large steam bath, a double boiler or a similar stove-top heating device.

In the canning or preserving of perishable food items, the particular items to be canned or preserved are first cooked or are otherwise subjected to elevated temperature. This process eliminates any bacteria that might have been present in the food items and renders these items safe for preservation. The heated food items are then placed, while in their heated condition, into suitable, sterilized canning jars. The jars are then covered with seals. The seals are then held in place on top of the glass jars by the tightening of screw threaded, jar neck engaging bands. The now canned food items are allowed to cool. As the contents of the jars cool, they will contract and will form a vacuum in the sealed jars. It is important that the evacuated area be free from contaminants. It is the inert evacuated head space that preserves the food product which has been canned or preserved. It is the sterility of the canning implements that insures the maintenance of that inert evacuated head space.

Canning jars, bands or rings and seals are typically sterilized by being placed in boiling water in a water bath or in a canning pot. Such a pot, or a similar double boiler, sits on the top of the stove and takes up a considerable amount of space. Since the food items or products which are to be canned, are also being kept at an elevated temperature, the result is a substantial reduction in the space on the stove top available for preparation of the food to be preserved.

The typical water bath or canning pot holds a substantial amount of hot water into which the canning jars, rings or bands, and seals are immersed. While it is not necessary to use hot water as the sterilization medium, it is the heat that accomplishes the sterilization. The seals are best kept moist to ensure that the resilient portion, which forms a seal with the jar neck finish, stays soft and pliable. Otherwise, dry heat would be just as effective in sterilizing the jars and bands. However, in stove top water bath pots or the like, the source of heat is the hot water in the pot. This large volume of hot water, in addition to taking up a large amount of otherwise usable space, is also a safety concern. If the pot is upset, the hot water poses a serious scalding hazard.

The canning jars, and their associated bands or rings and seals are placed in the water bath or canning pot, typically in some type of rack. When it is desired to use a jar, the rack must be elevated out of the pot and the jar then removed. Again, there is a potential risk involved with the use of such a large volume of hot water. Alternatively, a single jar may be removed from the boiling water by the use of a pair of tongs, tweezers, or other similar gripping tool. That procedure is cumbersome and essentially requires the user to attempt to grasp articles which are not readily visible.

If the typical water bath or canning pot were not required for sterilization of the canning jars, bands, and seals, there would be made available at least one additional burner element on the stove top. This at least one additional burner could be used to prepare the food products that are to be canned. Even if the stove top element required to heat the water bath or other pot were not used instead to heat food products being prepared for canning, there would simply be more space available to undertake the cooking activities.

It will thus be seen that a need exists for a canning implement sterilization rack that overcomes the limitations of the prior devices. The oven-supportable canning implement sterilization rack in accordance with the present invention overcomes these limitations of the prior art. It is a substantial advance over the prior art.

SUMMARY OF THE INVENTION

It is an object of the present invention to provide a canning implement sterilization rack.

Another object of the present invention is to provide an oven-supportable canning implement sterilization rack.

A further object of the present invention is to provide a size-adjustable, oven-supportable canning implement sterilization rack.

Yet another object of the present invention is to provide a canning implement sterilization rack that supplies both wet and dry heat to selected ones of the canning implements.

Still a further object of the present invention is to provide a canning implement sterilization rack which will keep the various implements physically separated and easily accessible.

An even further object of the present invention is to provide a canning implement sterilization rack that is durable, safe and easy to use.

The oven-supportable canning implement sterilization rack in accordance with the present invention includes three separate areas, each specifically structured to hold-one of the three typical canning implements or components. The rack includes a canning jar receiving grid or openwork which is sized to support and to keep separate a plurality of canning jars of various sizes. This grid or openwork insures that each of the jars is adequately supported, while still allowing easy removal and placement of the jars.

A band or ring receiving compartment or receptacle is included in the rack. It is configured to receive a number of bands or rings that are usable, in a known manner, to secure seals onto the mouths of the canning jars, once the jars have been filled. The jar receiving grid and the band receiving compartment are subjected to dry heat during the sterilization process.

A water bath is also part of the canning implement sterilization rack of the present invention. The water bath includes a removable top and allows a plurality of seals to be immersed in hot water to a depth sufficient to completely cover the seals. The resilient portions of each of the seals thus stays moist. A suitable tool can be provided to accomplish the retrieval of individual seals from the water bath.

The canning implement sterilization rack of the subject invention is placed in an oven, not on top of the stove, as has been done in the past. The sides of the rack are configured to be supported on the slide rails that conventionally support a typical oven rack. The canning implement sterilization rack of the present invention is width adjustable so that it can be used with various home ovens. It can also be made depth adjustable for use with various home ovens of different depths.

The canning implement sterilization rack uses no stove top space. It is placed in the oven and used the oven's heat to accomplish sterilization of the jars, bands and seals. The water bath is filled with water that is heated while the rack is supported in the oven. The seals are kept separate from the jars and bands and are immersed in the hot water in the water bath. While there is enough water in the water bath to keep the seals moist, there is not so much water that it poses a safety risk.

In comparison to the prior art water bath or canning pot, only the seals are sterilized by immersion in hot water in the course of the use of the canning implement sterilization rack of the present invention. The seal water bath is supported in the rack as a separate section of the rack. The amount of water required is greatly reduced. The likelihood of a spillage of the water is also great reduced. A lid or cover for the seal water bath is able to be removed so that the bath's contents can be accessed.

Each area or section of the oven-supportable canning implement sterilization rack, in accordance with the present invention, supports its own one of the several canning implements, fittings or compartments. The jars are held in their grid or openwork, the rings or bands are supported in their compartment, and the seals are kept moist in the waterbath. Each component can be selected and grasped easily. There is no need to attempt to locate the desired component or fitting in a large pot full of various components and boiling water. The sterilization rack of the present invention keeps each canning implement or component in its own area of the rack. These areas are separated and each is accessible. There is no need to grasp components at random from a pot of hot water.

The oven-supportable canning implement sterilization rack in accordance with the present invention overcomes the limitations of the prior art. It does not require stove top space, it does not present a hot water spillage hazard and it keeps the canning implements or components separated. It is adaptable to various sizes of ovens and is simple to use. It is a substantial advance in the art.

BRIEF DESCRIPTION OF THE DRAWINGS

A full and complete understanding of the oven-supportable canning implement sterilization rack in accordance with the present invention may be had by referring to the detailed description of the preferred embodiment, as set forth subsequently, and taken in conjunction with the accompanying drawings, in which.

DESCRIPTION OF THE PREFERRED EMBODIMENT

Figure 1:
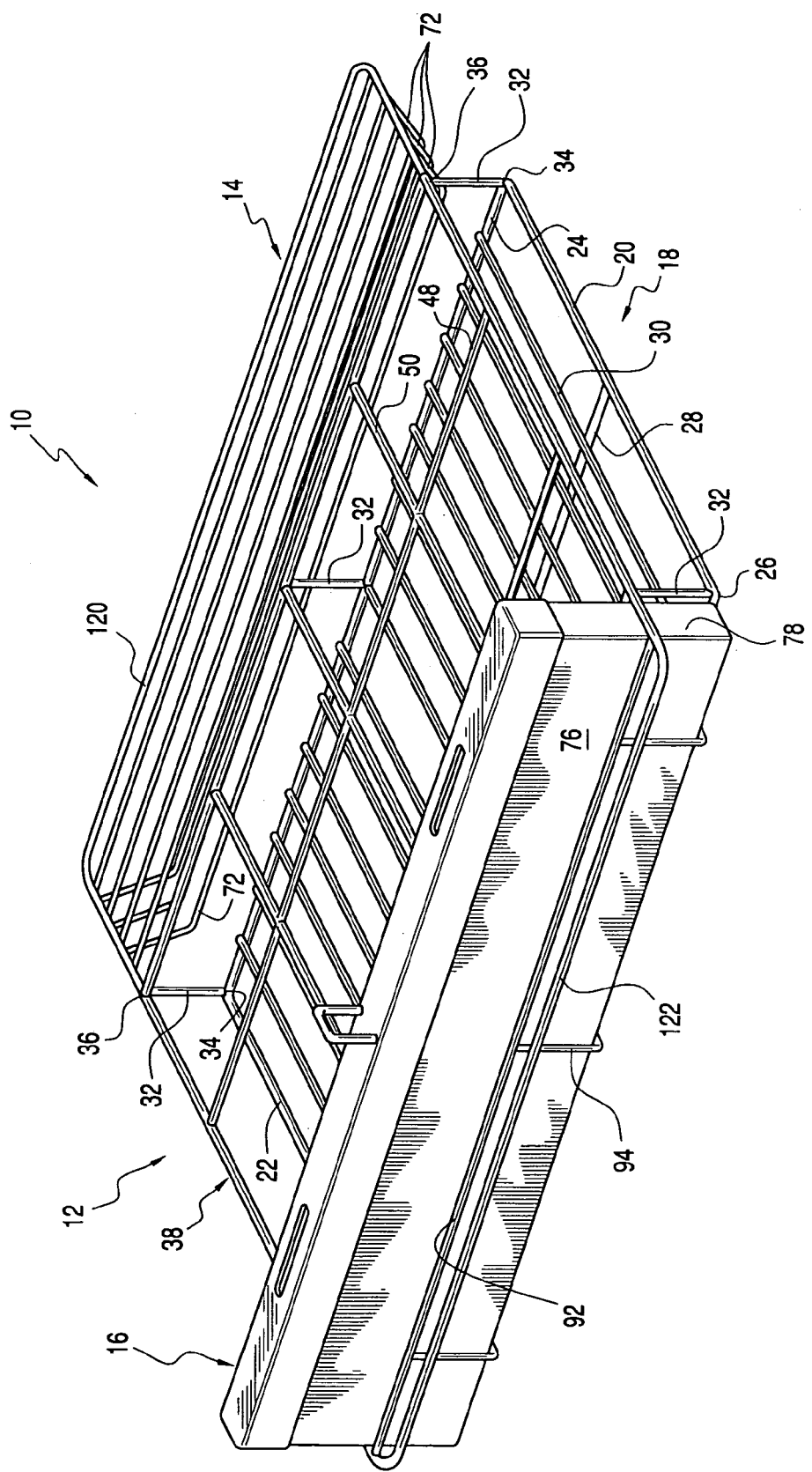
FIG. 1 is a perspective view of an oven-supportable canning implement sterilization rack in accordance with the present invention.

Referring initially to FIG. 1, there may be seen a preferred embodiment of an oven-supportable, canning implement sterilization rack, generally at 10, in accordance with the present invention. Sterilization rack 10 is comprised of three areas or sections, each of which is intended to support and to sterilize a particular canning implement. As seen in FIG. 1, the rack 10 includes a canning jar receiving grid 12, a ring or band receiving receptacle 14 and a seal sterilizing and moistening water bath 16.

The rack, generally at 10, is intended to be placed in a conventional oven so that the canning implements, such as the canning jars and their fittings, such as the well known bands or rings, and seals, which are depicted in dashed lines in FIG. 2, and which will be discussed shortly, can be sterilized by being placed in the rack which, in turn, is placed in an oven. The rack 10 is preferably made of stainless steel or of a similar material, such as is used to construct conventional oven racks. Other materials are also suitable for use, so long as they are able to stand up to lengthy exposure to the heat generated by a typical oven during the sterilization process.

Again referring to FIG. 1, and also as is shown in the several other drawing figures, rack 10 and specifically the jar receiving grid 12 has a lower support base 18. Base 18 is generally rectangular in plan view, as seen in FIG. 1 and includes a rectangular frame consisting of a front bar 20, a rear bar 22, a right side bar 24 and a left side bar 26. These four bars 20, 22, 24 and 26 define the rectangular shape of the support base 18. In a preferred embodiment, this support base is approximately 12⅛" wide and 16¾" deep. It will be understood that these sizes are given for purposes of illustration and are not intended to limit the size of the rack 10. It is to be understood that the rack 10 to be described hereinafter, is sized to be receivable in a conventional oven. Other sizes of similar racks could be made in accordance with the sizes of the particular oven with which they are intended to be used.

The support frame of the lower support base 10, defined by the four bars 20, 22, 24 and 26, is provided with a central support beam 28. This support beam 28 is parallel to the right and left side bars 24 and 26, respectively and is attached to the front and rear bars 20 and 22 by any suitable method, such as spot welding or brazing. Support beam 28 is depicted in FIG. 1 as being spaced equidistant the two side bars 24 and 26. It is apparent that the support base 18 could have more than one support beam 28. Several equally spaced support beams 28 could alternatively be used, if desired.

A plurality of equally spaced cross bars 30 are supported by the right and left side bars 24 and 26, respectively of the support base 18, and the central support beam 28. These cross bars 30 are equally spaced from each other and from the front and rear bars 20 and 22, respectively and are parallel thereto and to each other. In practice, the front and rear bars 20 and 22, the right and left side bars 24 and 26, the central support beam 28 and the spaced cross bars 30 are all made of stainless steel rods of ¼ inch diameter. They are all spot-welded together or are otherwise joined to form the support base 18. Since their purpose is to provide support for a plurality of empty canning jars, as will be discussed shortly, and to also stabilize the rack 10, they must be rigid but need not be so large as to be cumbersome.

Figure 2:
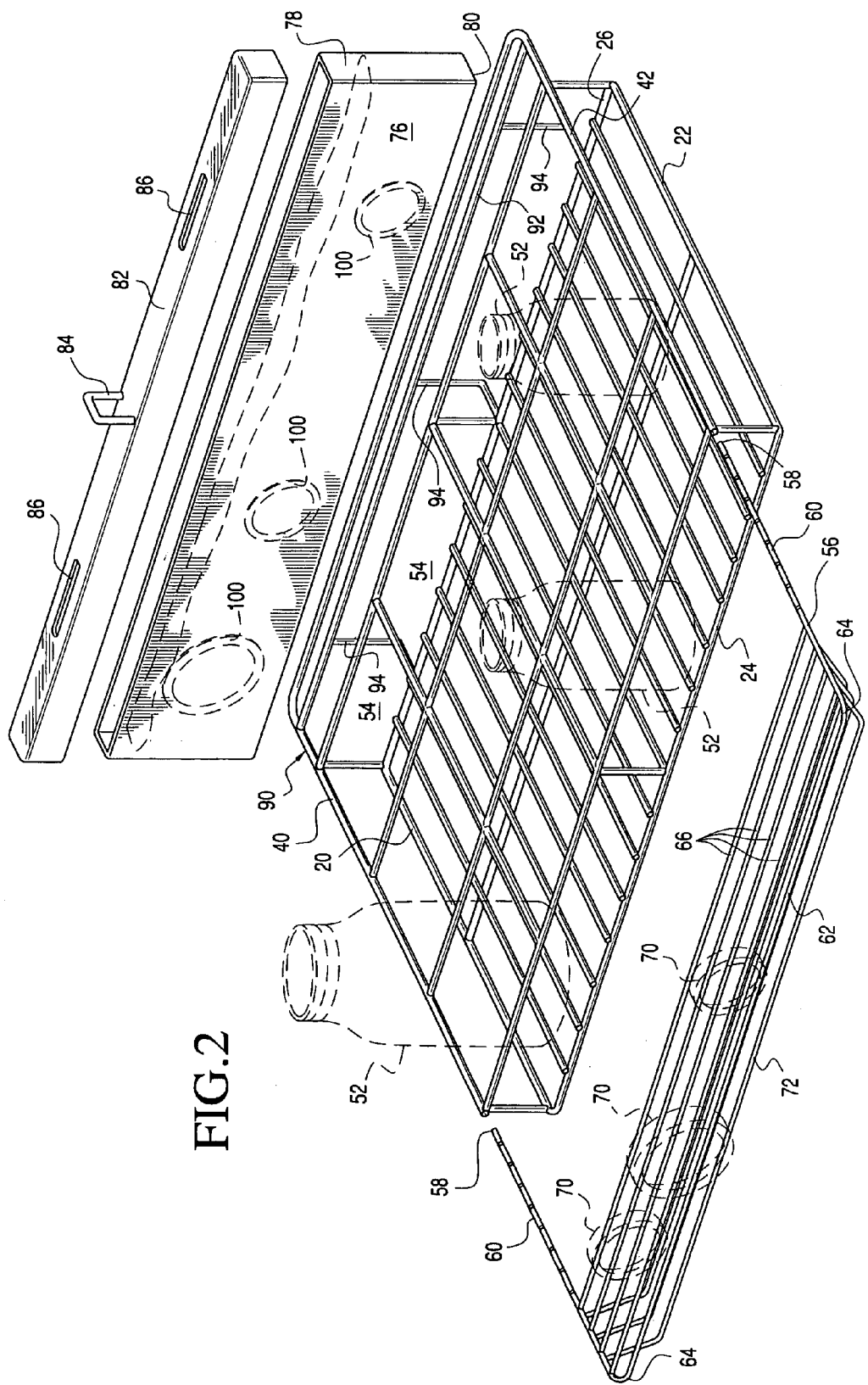
FIG. 2 is an exploded perspective view of the sterilization rack and showing the various components of the rack separated.
Figure 3:
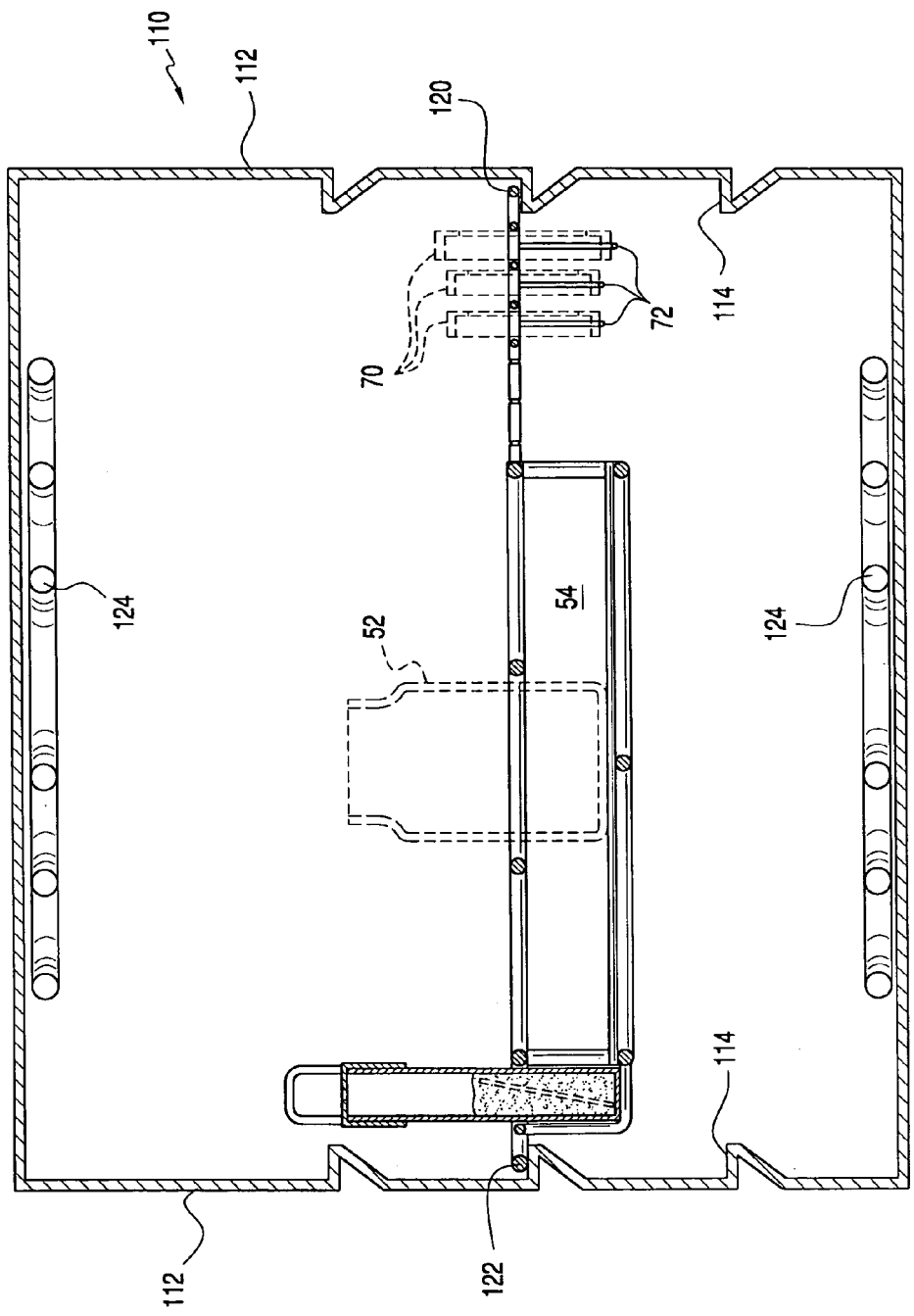
FIG. 3 is a cross-sectional, side elevation view of the oven-supported, canning implement sterilization rack, taken along line 3-3 of FIG. 4, and showing the rack in its use position in an oven.

Riser bars 32 extend upwardly from the four corners of the support base 18, as is also seen in FIGS. 1-3. These riser bars 32 are connected, at lower ends 34, to the support base 18 and extend upwardly two inches. These riser bars 32 are also typically of stainless steel and are spot welded, or otherwise permanently joined at their lower ends 34 to the lower support base 18. The riser bars 32 have upper ends 36 which are used to support an upper gridwork 38 portion of the canning jar retainer grid 12.

This open, upper gridwork 38 consists of front and rear grid rods 40 and 42, respectively; right and left grid rods 44 and 46, respectively and longitudinal and transverse grid rods 48 and 50, respectively. These cooperate to define a generally rectangular open gridwork 38 which is supported above, and spaced from the lower support base 18 by the riser bars 32. The upper open gridwork 38 is parallel to, and of the same overall size, as the lower support base 18.

Figure 4:
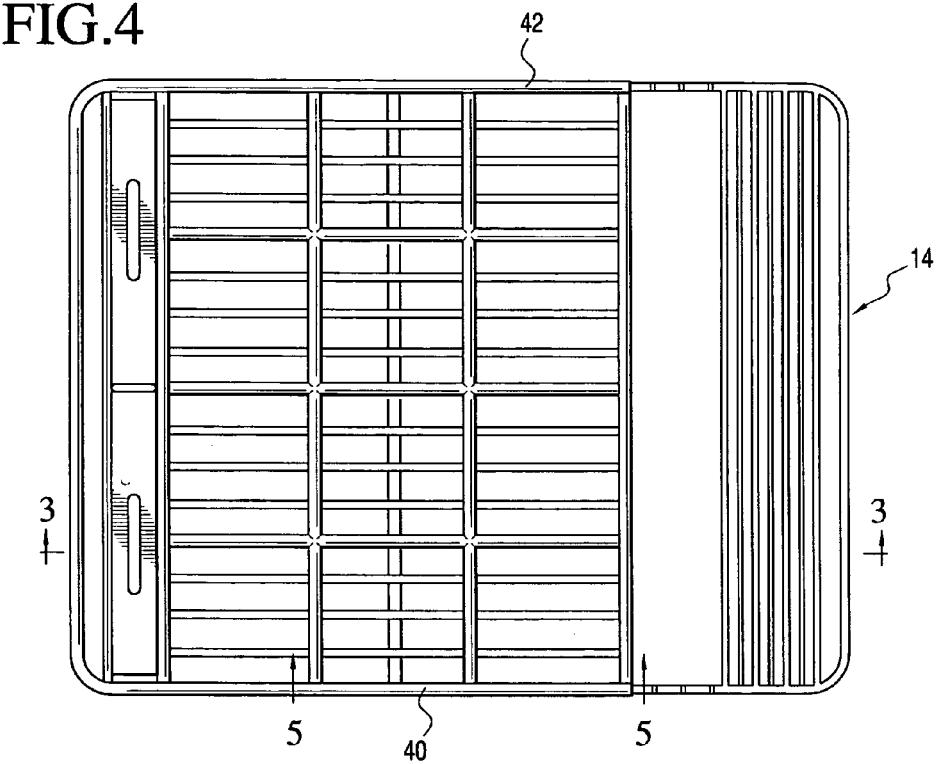
FIG. 4 is a top plan view of the rack.

As may be seen more clearly in FIGS. 2 and 3, the canning jar receiving grid 12, that is formed by the lower support base 18 and the spaced upper gridwork 38, is sized to receive a plurality of canning jars, generally at 52, of varying sizes. These canning jars 52 typically are available in quart, pint, and half-pint sizes. It will be understood that the apertures in the upper gridwork 38 are sized to accept these various capacity canning jars 52. It will also be understood that the lower support base 18 cross bars 30 are sufficient in number and are spaced so that they provide stable support for even the smallest of the canning jars 52 with which the rack 10 is contemplated for use. In a preferred embodiment, as depicted in FIGS. 1, 2 and 4, there are 12 such canning jar receiving apertures 54 defined by the upper gridwork 38. These apertures 54 are depicted as each being square. They could be rectangular, circular or the like, if desired. It is intended that the apertures be sized so that the canning jars 52 will not contact each other and will not necessarily contact the various grid rods 40, 42, 44, 46, 48 and 50. The provision of twelve canning jar receiving apertures 54, as depicted in FIGS. 1, 2, 3 and 4 is a function of the overall size of the rack 10. If the rack 10 is intended for use with a different sized oven, it will be apparent that the overall size of the canning jar receiving grid, generally at 12, can be changed. That change in overall size of the canning jar receiving grid, generally at 12 may affect the number of canning jar receiving apertures 54 in the upper gridwork 38.

Referring again to FIG. 1 and taken in conjunction with FIG. 2, the band receptacle 14 is supported along one side of the jar receiving grid 12 and extends in the longitudinal direction of the rack. In the rack depicted in FIG. 1, the band receptacle 12 is on the right side of the grid 12 and the seal water bath 16 is on the left. These positions could be reversed. The receptacle 14 and the water bath 16 could also be adapted to each be supported on either side of the central grid 12, as will be discussed in detail subsequently.

Figure 5A:
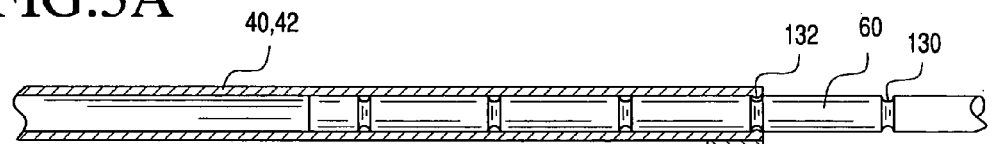
FIGS. 5A, 5B and 5C are cross-sectional views, taken along lines 5-5 of FIG. 4, and showing several configurations for adjusting the width of the sterilization rack of the present invention.
Figure 5B:
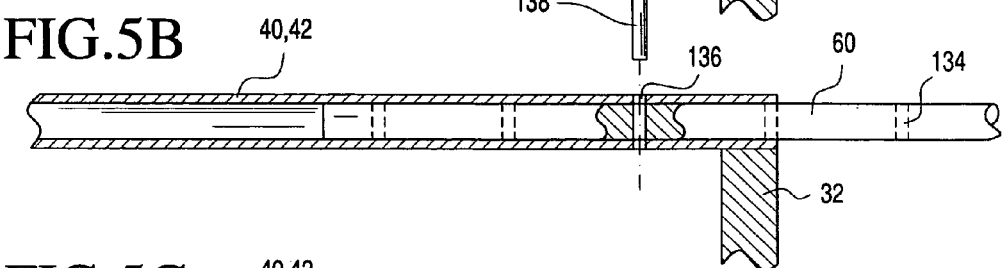
Figure 5C:
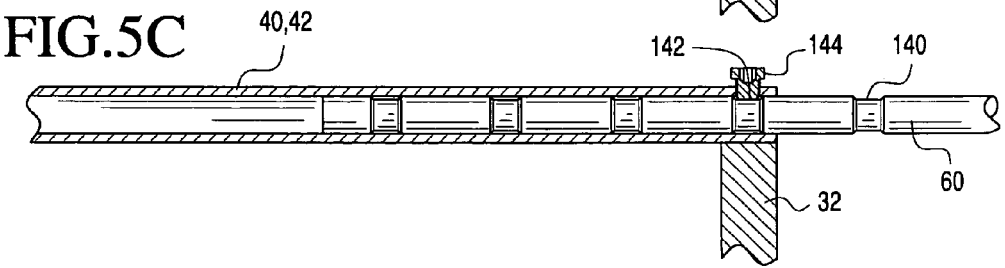

The band receptacle, generally at 14 includes a generally U-shaped receptacle frame 56, as seen most clearly at FIG. 2. Distal ends 58 of the frame side legs 60 are telescopingly receivable in the front and rear grid rods 40 and 42, which, as seen in FIGS. 5A, 5B and 5C are hollow. The telescoping engagement will be discussed in detail subsequently.

Band receptacle frame 56 also has a frame cross leg 62 which extends between proximal ends 64 of the two spaced frame side legs 60. The two frame side legs 60 and the frame cross leg 62 define the generally U-shaped band receptacle frame 56.

As seen most clearly in FIGS. 1, 2 and 4, a plurality of spaced divider bars 66 are situated at the end of the U-shaped receptacle frame 56, adjacent to, and spaced from the frame cross leg 62. These divider bars 66 are welded or are otherwise attached to the proximal portions 64 of the two frame side rails 60 and are generally perpendicular thereto. These divider bars 66 are spaced from each other at a spacing width that is greater than a width of a canning ring or band 70, several of which are shown in dashed lines in FIGS. 2 and 3 as being supported in the band receiving receptacle 14.

A plurality of ring or band support channels 72 are also secured to the proximal portion 64 of the frame side legs 60 of the U-shaped receptacle frame 56. As seen in FIGS. 1-4 these support channels 72 are supported beneath, and are interposed between the spaced divider bars 66. While the divider bars 66 engage the rings or bands 70 and essentially keep them separated from each other, the support channels 72 support the bands 70 as they are placed on their sides or ends in the band or ring receiving receptacle 14. The channels 72 can be of uniform depth, as depicted in FIGS. 1 and 2. Alternatively, they can be of varying depths, as depicted in FIG. 3. The use of varying depth channels 72 elevate the smaller diameter ones of the rings or bands, which are used with the pint and half-pint canning jars 52. In either depth, the support channels 72 are attached to the proximal portions 64 of the frame side legs 60 by any suitable method, such as welding. These channels are typically ¼ inch stainless steel and in a preferred embodiment, as depicted in FIGS. 1, 2 and 3 there can be three parallel elongated band or ring support receptacle areas in the band receiving receptacle 14.

Referring again to FIGS. 1 and 2, the rack 10 is also provided with a seal receiving water bath, generally at 16. Water bath 16 is, in the preferred embodiment, a generally oblong bath 74 which is constructed of spaced bath side walls 76, bath end walls 78 and a bath bottom wall 80. The bath 74 is generally five inches in height, one inch wide and sixteen and three-fourth inches long. A removable bath lid 82 is sized to fit over the open mouth of the bath 74. The bath lid 82 includes a central lid handle 84 and a pair of spaced bath lid vent openings 86.

The seal water bath 14 is supported in a water bath cradle 90 which is formed as an extension of the front and rear grid rods 40 and 42, in cooperation with a cradle side rail 92 and at least three downwardly extending cradle legs 94. The cradle legs 94 extend between the cradle side rail 92 and the left side bar 26 of the lower support base 18 of the canning jar receiving grid 12.

In use, the water bath 74 is partially filled with water. A plurality of seals, generally at 100, which are generally conventional, and which are shown in dashed lines in FIG. 2, are immersed in the water in the bath 74. When the rack 10 is placed in an oven, as is depicted in FIG. 3, the heat from the oven will keep the water in the bath 74 hot and will sterilize the seals 100. The water also keeps the resilient rings, which are a component of each seal, moist.

Again referring to FIG. 3, the canning implement sterilization rack, generally at 10, in accordance with the present invention, is intended to be placed in an oven generally at 110. Oven 110 is structured with side walls 112 that have conventional slide rails 114 which are typically used to support oven racks which can slide into and out of the oven on the slide rails 114. The canning implement sterilization rack, generally at 10, is supportable in oven 110 through the provision of rack slide bars 120 and 122. Rack slide bar 120 is located, as seen in FIGS. 1-3, on the band receiving receptacle 14 and is formed by the frame cross leg 62. It would be possible to provide cross leg 62 and right side rack slide bar 120 as separate elements. Preferably, they are the same. The left side rack slide bar 122 is located outboard of the waterbath cradle side rail 92. In use, as depicted in FIG. 3 the rack 10 is slideable into the oven 110 with the rack slide bars 120 and 122 being supported by the oven slide rails 114. When the rack 10 is in the oven, the oven's heating element 124 are usable to heat the rack and its contents, as will be discussed shortly.

Conventional home ovens 110 are not all the same width or depth. It is thus essential that the width of the rack 10 is adjustable so that the rack can be used in a variety of ovens of varying widths. As was discussed briefly above, the rack 10 is width adjustable through the provision of a telescoping cooperation between the frame side legs 60 of the band or ring receiving receptacle 14 and its hollow front and rear grid rods 40 and 42, respectively, of the canning jar receiving grid 12. As may be seen most clearly in FIGS. 5A, 5B and 5C, the frame side legs 60 are sized to fit into the hollow front and rear grid rods 40 and 42.

FIGS. 5A, 5B and 5C depict several possible means for adjusting the location of the frame side legs 60 in the grid rods 40, 42. As seen in FIG. 5A, the frame side legs 60 can have a plurality of spaced annular grooves 130. The grid rods 40 and 42 can be provided with inwardly directed detents 132. The cooperation of the grooves 130 and the detents 132 will provide a number of positions for the positioning of the band receiving receptacle 14 with respect to the jar receiving grid. Alternatively, as seen in FIG. 5B, the frame side legs 60 can have a plurality of spaced bores 134 and the grid rods 40, 42 can have apertures 136 and pins 138. The bores 134 can be aligned with the apertures 136, and the pins 138 can be inserted through the aligned apertures 136 and bores 134. In the third depicted configuration, the frame side legs 60 can have larger annular bands 140 and the grid rods 40, 42 can have threaded apertures 142. Thumb screws or set screws 144 are received in the threaded apertures 142 and can be screwed down into engagement with the bands 140. If desired, the bands 140 can be omitted and the set screws 144 can be screwed down to engage the frame side legs 60 at any point. This will provide an infinite range of width adjustment for the rack 10. In the preferred embodiment, the rack 10 has a width of 18 inches and depth of 16¾ inches. The width can be increased by 12 inches through telescopic movement of the band receiving receptacle 14 with respect to the jar receiving grid 12.

It would also be possible to adjust the depth of the rail in a generally similar fashion. This would require the use of a number of telescoping elements cooperating with each other. Alternatively the rack 10 could be fabricated in several size ranges, one of which would be suitable for use with smaller ovens. It is also within the scope of the present invention to support the water bath cradle 90 so that it could also be telescoping with respect to the jar receiving grid 12. Further, the water bath cradle 90 and the U-shaped band or ring receptacle frame 14 could be structured so that each would be supportable on either side of the center jar receiving grid 12. This would require the modification of selected ones of the lower support base cross bars 30 to be hollow so that they could receive the ends of the base portion of the L-shaped cradle legs 94.

In use, the oven-supportable canning implement sterilization rack, generally at 10, in accordance with the present invention is initially adjusted to the proper width, based on the width of the oven into which it will be placed. The water bath 74 is filled with sufficient water to cover the seals 100 which will be placed in it, and is positioned in the water bath cradle 90. The various canning jars, bands or rings, and seals are washed separately and are placed in the rack 10. The jars are placed in the apertures 54 in the jar receiving grid 12; the rings or bands are placed in the slots in the band receiving receptacle 14 and the seals are placed in the water bath 74. The cover 82 is placed on the bath 74 and the filled rack is placed in the oven.

The oven is heated to an elevated temperature, and is held at that temperature for a sufficient time to sterilize the jars, bands and seals. The oven can then be turned off and the rack can be left in the oven. When it is desired to use one of the jars, bands, and seals, they can be individually removed from their separate area of the rack. If desired, a suitable tool, what is not specifically shown, could be used to remove the canning components. The tool would preferably be tong-like and would be made of stainless steel and have a length of approximately 14 inches. The two arms of the tool would be pivotably connected to each other at first ends and would have magnetic portions at their opposing, free ends. The tongs or tool can be used to remove seals from the water bath; to remove jars from the grid, and to remove bands from the receptacle. When the tool is not in use, it can be placed on top of the water bath cover, extending through the handle 84.

In the above description of the preferred embodiment, the rack 10 has been discussed as having been made of stainless steel materials which are generally in the shape of tubes and/or rods. Other materials, which will tolerate being heated in an oven, and which will not react with the jars, rings, or bands, and seals could also be used. In addition, the various tubes, rods and the like could be made of thin, flat stainless steel or other similar material. Not all of the structural elements need to be of the same size. While the rack needs to have sufficient structural rigidity to accomplish its task, it does not have to support a great deal of weight, thus the specific rod sizes set forth are to be understood as being exemplary of the type and size of elements that could be used.

While a preferred embodiment of an oven supportable canning implement sterilization rack, in accordance with the present invention, has been set forth fully and completely hereinabove, it will be apparent to one of skill in the art that various changes in, for example, the overall size of the rack, the number of jars that can be supported by the rack, the type of jars, bands and seals that can be used in the rack and the like can be made without departing from the true spirit and scope of the subject invention which is accordingly to be limited only by the following claims.

What is claimed is:

1. An oven-supportable canning implement sterilization rack comprising:
    a canning jar receiving grid;
    a canning jar band receiving receptacle secured to a first side of said grid and having at least one band support area;
    a water bath receiving cradle secured to a second side of said grid opposite to said first side; and a water bath adapted to receive canning jar seals and being removably supportable in said water bath receiving cradle and adapted to receive water usable to sterilize said canning jar seals positionable in said water bath.

2. The rack of claim 1 wherein said canning jar receiving grid includes a support base and an open gridwork positioned above said support base.

3. The rack of claim 2 wherein said support base and said open gridwork cooperate to define a plurality of canning jar receiving apertures in said canning jar receiving grid.

4. The rack of claim 3 wherein all of said apertures are the same size.

5. The rack of claim 3 wherein said plurality of apertures include at least first and second apertures having first and second sizes different from each other and wherein said at least first and second apertures are adapted to receive canning jars of different capacities.

6. The rack of claim 1 wherein said band receiving receptacle includes a generally u-shaped frame.

7. The rack of claim 6 wherein said band receiving receptacle frame has a pair of frame side legs and a frame cross leg.

8. The rack of claim 7 further including a plurality of divider bars extending between said frame side legs, and a plurality of band support channels also extending between said frame side legs, said divider bars and said band support channels cooperating to define a plurality of said band support areas.

9. The rack of claim 1 wherein said water bath includes a removable cover.

10. The rack of claim 2 wherein said water bath receiving cradle is attached to said second side of said grid and said band receiving receptacle is attached to said first side of said grid and adjacent said open gridwork.

11. The rack of claim 1 further including means on said rack adapted to support said rack in an oven.

12. The rack of claim 11 wherein said means on said rack includes spaced rack slide bars, said rack slide bars being adapted to be supported by slide rails of an oven.

13. The rack of claim 12 wherein one of said spaced rack slide bars is part of said band receiving receptacle and another of said spaced rack slide bars is part of said water bath receiving cradle.

14. The rack of claim 1 further including means on said rack for varying a width of said rack.

15. The rack of claim 1 wherein said grid includes hollow grid rods and said band receiving receptacle includes spaced frame side legs, each of said spaced frame side legs being telescopingly receivable in a respective one of said hollow grid rods.

16. The rack of claim 15 further including means securing said telescoping frame side legs at a defined position in said hollow grid rods.

17. The rack of claim 16 wherein said securing means includes annular grooves on said side legs and detents on said grid rods.

18. The rack of claim 16 wherein said securing means includes bores in said side legs and apertures in said grid rods, and further including pins receivable in aligned ones of said bores and apertures.

19. The rack of claim 16 wherein said securing means includes a threaded aperture in each of said grid rods and a thumb screw receivable in each said threaded aperture and engageable with said side leg received in each said grid rod.

20. The rack of claim 9 further including a handle on said cover and at least one vent opening in said cover.

21. An oven-supportable canning implement sterilization rack comprising:

a canning jar receiving grid;

a band receiving receptacle secured to said grid, said band receiving receptacle including a first rack slide bar;

a water bath receiving cradle secured to said grid, said water bath receiving cradle including a second rack slide bar spaced from said first rack slide bar; and a water bath adapted to receive canning ear seals and being removably supportable in said water bath receiving cradle and adapted to receive water usable to sterilize said canning jar seals positionable in said water bath, said first and second spaced rack slide bars being adapted to be supported by slide rails of an oven and to support said rack in the oven.

* * * * *